United States Patent
Park et al.

(10) Patent No.: US 7,972,634 B2
(45) Date of Patent: Jul. 5, 2011

(54) GEL-TYPE BIRD AVERSION COMPOSITIONS

(75) Inventors: Byung-Kwon Park, Daejeon (KR); Tae-Hun Lee, Daegu (KR); Hyuck-Jun Park, Daegu (KR); Jong-Hwan Lim, Daejeon (KR); Myoung-Seok Kim, Seoul (KR); Youn-Hwan Hwang, Daejeon (KR); In-Bae Song, Ulsan (KR); Seung-Chun Park, Daegu (KR); Joo-Heon Hong, Daegu (KR); Hee-Kyoung Jung, Daegu (KR); Mi-Hyun Hwang, Gimcheon-si (KR); Hyo-In Yun, Daejeon (KR)

(73) Assignee: Jeon Jin Bio Co., Ltd., Daegu (KR)

( * ) Notice: Subject to any disclaimer, the term of this patent is extended or adjusted under 35 U.S.C. 154(b) by 129 days.

(21) Appl. No.: 12/532,818

(22) PCT Filed: May 26, 2008

(86) PCT No.: PCT/KR2008/002936
§ 371 (c)(1),
(2), (4) Date: Sep. 23, 2009

(87) PCT Pub. No.: WO2008/147087
PCT Pub. Date: Dec. 4, 2008

(65) Prior Publication Data
US 2010/0104672 A1   Apr. 29, 2010

(30) Foreign Application Priority Data

May 28, 2007   (KR) .................. 10-2007-0051342

(51) Int. Cl.
*A01N 65/00* (2009.01)
(52) U.S. Cl. ..................................................... 424/725
(58) Field of Classification Search .................. None
See application file for complete search history.

(56) References Cited

FOREIGN PATENT DOCUMENTS

| | | |
|---|---|---|
| JP | 57-054105 | 3/1982 |
| KR | 1020030050331 | 6/2003 |
| WO | WO 94/16559 | 8/1994 |

*Primary Examiner* — Michael Meller
(74) *Attorney, Agent, or Firm* — IPLA P.A.; James E. Bame

(57) ABSTRACT

A gel-type bird aversion composition consists of, on the basis of weight, 30 to 90% of a thickening agent, 0.01 to 4% of an ultraviolet ray absorbent, 0.1 to 20% of methyl anthranilate, 0.1 to 10% of cinnamon essential oil, 0.1 to 20% of mint essential oil; 5 to 40% by weight of mineral oil or grease; and 1 to 10% by weight of emulsifier.

1 Claim, 2 Drawing Sheets

[Figure 1]
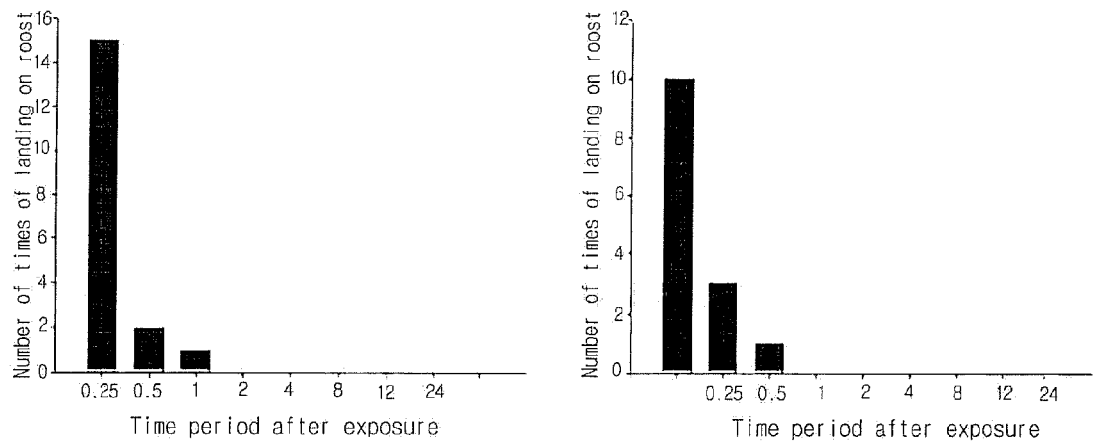
[Figure 2]
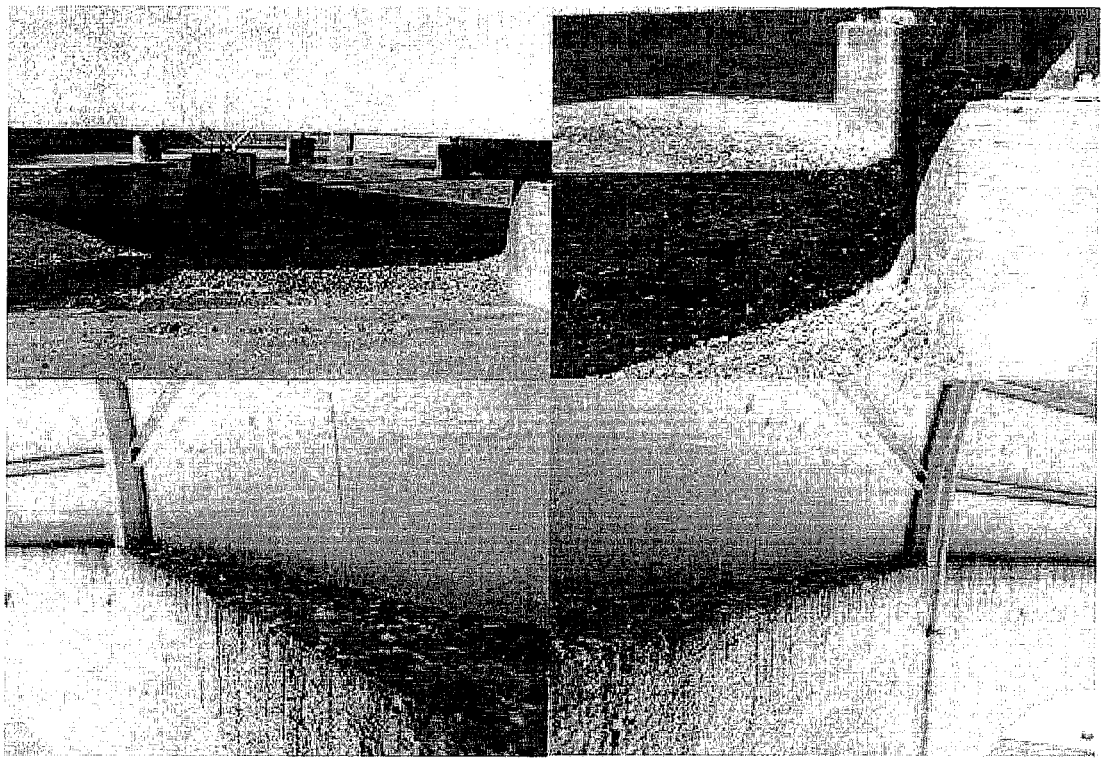

[Figure 3]
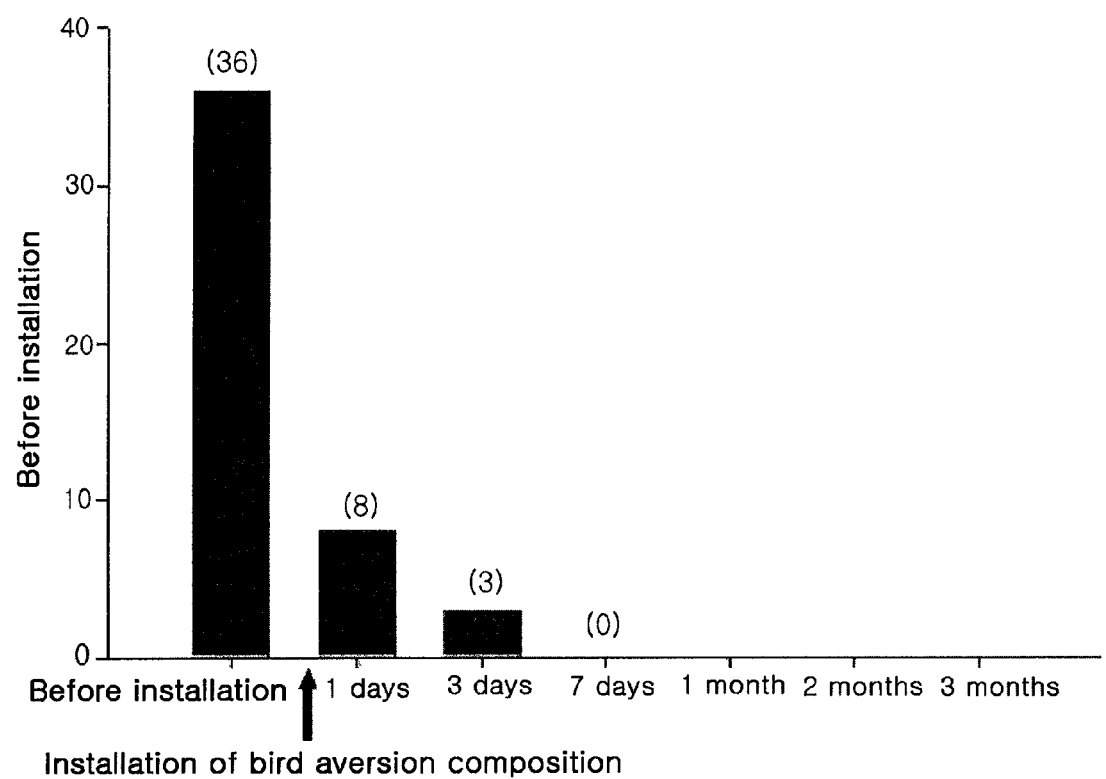

GEL-TYPE BIRD AVERSION COMPOSITIONS

TECHNICAL FIELD

The present invention relates to eco-friendly gel-type bird aversion compositions including contain nonfatal material, which is composed of main ingredients containing a thickening agent, an ultraviolet ray absorbent, methyl anthranilate, cinnamon essential oil and mint essential oil, and accessory ingredients containing mineral oil or grease and emulsifier.

BACKGROUND ART

In general, wild birds having coexisted with human beings for a long time have gone through the highly changed habitats by urbanization and industrialization followed by the development of civilization. Thus, specific birds are gradually decreased to become rare birds, species to be protected, but other birds are gradually increased as they are adapted to a change of environment.

Damages caused by birds, which were slight or seldom problematic in the past, have become more severe and even extended to a social problem. For example, damages to electric poles, airports, fish farms, bee farms, residential districts and other buildings as well as agricultural products are increasing step by step.

There are bird aversion methods used in protecting crops and facilities from harmful birds. These bird aversion methods employ: visual threatening products using a natural enemy model, a reflex mirror, a glittering tape, or the like; auditory aversion products using alarm sound, noise of radio or ultrasonic waves; contact products such as a protection net, a protection bag, a protection cap and the like; and products such as pasture liquid, naphthalene, methyl anthranilate, anthraquinone, and the like, which are mainly used in fruit farms.

While theses methods are used for exterminating birds giving harm to fruits, trees and facilities, they have lots of disadvantages such as a short-term effect and high cost and the like.

Bird aversion agents used for protecting crops and facilities from harmful birds are classified into primary and secondary bird aversion agents. The primary bird aversion agent is a formulation that is immediately able to prevent approaching of the birds by means of sight, taste, smell, stimulation and the like, and it does not need any learning effect.

The secondary bird aversion agent is also a formulation that causes pain by taking in foods and prevents ingestion of crops using a learning effect. Therefore, the secondary bird aversion agent is a material that leads to abnormal physiological and metabolic reaction when it is taken in, and exerts a unique effect only on harmful birds.

However, most of secondary bird aversion agents are agricultural chemicals or other chemicals, which have a latent problem causing environmental pollution and phosphorous-accumulated toxicity and the like due to their residuals. Further, the primary bird aversion agent has a disadvantage in that it usually has a slower durability effect than secondary bird aversion agent.

Recently, two types of bird aversion agents have been jointly used. Moason, et al. (1983) reported that effective bird aversion effects could be obtained when several chemicals or visual bird aversion compositions are added to methiocarb as secondary bird aversion agent. In addition, the combination of such primary bird aversion agent allows the effective concentration of secondary bird aversion agent to be remarkably reduced.

Therefore, there is an increasing need for development of an effective, eco-friendly bird aversion agent that can complement disadvantages of the conventional bird aversion agent.

DISCLOSURE

Technical Field

The present invention has been made to solve the foregoing problems with the prior art, and therefore an object of the present invention is to provide gel-type bird aversion compositions using eco-friendly, non-fatal chemicals.

Technical Solution

According to an aspect of the present invention, a gel-type bird aversion composition includes 30 to 90% by weight of a thickening agent, 0.01 to 4% by weight of an ultraviolet ray absorbent, 0.1 to 20% by weight of methyl anthranilate, 0.1 to 10% by weight of cinnamon essential oil, 0.1 to 20% by weight of mint essential oil, 5 to 40% by weight of mineral oil or grease; and 1 to 10% by weight of emulsifier.

The thickening agent may be polybutene.

The ultraviolet ray absorbent may be one selected from the group consisting of benzophenones, benzotriazoles, salicylates, cyanoacrylates and oxanilides.

The emulsifier may be sorbitan esters of fatty acids.

Advantageous Effects

As set forth above, the gel-type bird aversion compositions of the present invention are convenient formulations in gel-type applicable to electric poles, building piers and aerodromes contaminated severely by harmful birds to form oil films. The oil films formed on the applied layer may prevent from lowering of effects of the bird aversion compositions due to temperature variation and moisture, and thus a long-term bird aversion effect can be acquired.

DESCRIPTION OF DRAWINGS

FIG. 1 shows the number of times of landing attempts of a zebrafinch(A) and a Bengalee(B) on the roost applied with the bird aversion composition according to the present invention.

FIG. 2 shows the actual states of buildings contaminated by excrements of doves.

FIG. 3 shows the number of homing doves before or after installation of the bird aversion composition as time goes on.

BEST MODE

In order to complete the above objects, the present invention provides a gel-type bird aversion composition containing 30 to 90% by weight of a thickening agent; 0.01 to 4% by weight of an ultraviolet ray absorbent; 0.1 to 20% by weight of methyl anthranilate; 0.1 to 10% by weight of cinnamon essential oil; 0.1 to 20% by weight of mint essential oil; 5 to 40% by weight of mineral oil or grease; and 1 to 10% by weight of emulsifier.

Now, the present invention will be described in greater detail.

The thickening agent as one of main ingredients is a polymer containing at least one of butene polymer and copolymer, and is mostly composed of the butene polymer or the copolymer.

The butene polymer or the copolymer may be polybutene, which is a mixture of high molecular weight polymer and low molecular weight polymer. The polybutene is a thickening agent registered with US FDA and EPA as a food additive, and is known to have a bird aversion effect by irritating a sense of touch by stickiness.

However, the polybutene has low stability to a change in temperature, and insufficient durability of the aversion effect. Thus, the polybutene is disadvantageous for a climate condition in which temperature and rainfall are seriously changed through the year.

The inventors of the present invention have developed a bird aversion composition using a thickening agent causing stickiness as a base material of the gel-type bird aversion composition to maximize the bird aversion effect, and using other main ingredients jointly to increase its stability.

The thickening agent is used within a range from 30 to 90% by weight, and preferably a range from 40 to 70% by weight on the basis of the total weight of the composition.

At this time, if the thickening agent is used in an amount equal to or less than 30% by weight per the total weight of the composition, then the viscosity is reduced to decrease the bird aversion effect. In contrast, if the thickening agent is used in an amount equal to or greater than 90% by weight, then the bird aversion effect can be increased, but its loss, denaturation and decrease of combination effect with other ingredients may be caused in a climate condition in which temperature and rainfall are seriously changed through the year.

The ultraviolet ray absorbent as one of main ingredients of the present invention has an effect of making it possible for the birds to sense an area treated with the bird aversion agent in the distance, because the birds can sense an ultraviolet ray region. Further, the ultraviolet ray absorbent can maximize the aversion effect on the corresponding area by reminding the birds of unpleasant feeling caused by ingestion or contact of the bird aversion agent.

The ultraviolet ray absorbent used for the present invention is selected from the group consisting of benzophenones, benzotriazoles, salicylates, cyanoacrylates and oxanilides, and preferably benzotriazoles.

The ultraviolet ray absorbent is be used within a range from 0.01 to 4% by weight per the total weight of the composition, and preferably a range from 0.1 to 2% by weight.

At this time, if the ultraviolet ray absorbent is used in an amount equal to or less than 0.01% by weight per the total weight of the composition, then an effect of absorbing ultraviolet rays is weak. Moreover, even if the ultraviolet ray absorbent is used in an amount equal to or greater than 4% by weight, it is not observed that the bird aversion effect is remarkably increased.

The methyl anthranilate as one of main ingredients of the present invention is pale or dark yellow liquid having grape flavor, orange flavor and neroli oil flavor, and is an extract from Concord grape. The methyl anthranilate is a food additive registered with US EPA, and is known to irritate eyes, nasal cavity or mucous membrane when the birds take it in.

The bird aversion agent consisting essentially of methyl anthranilate has already been commercialized, but has drawbacks in that the intensity of stimulation is relatively weak and that the durability of the effect has a relatively short range from 6 to 7 days.

According to the present invention, in order not only to overcome the disadvantage of the methyl anthrenilite but also maximize the effect of stimulating birds eyes or mucous membrane in nasal cavity, the methyl anthrenilite is combined with other main ingredients, which leads to a bird aversion composition.

The methyl anthranilate is used within a range from 0.2 to 20% by weight per the total weight of the composition, and preferably a range from 2 to 8% by weight.

At this time, if the methyl anthranilate is used in an amount equal to or less than 0.2% by weight per the total weight of the composition, then the bird aversion effect is not showed. In contrast, if the methyl anthranilate is used an amount equal to or greater than 20% by weight, it may cause a problem with toxicity.

The cinnamon essential oil as one of main ingredients of the present invention contains cinnamic aldehyde and cinnamic acid as main active ingredients, and it may represent an osmatic aversion effect caused by irritable volatile scents as well as an aversion effect caused by stimulation of mucous membranes in eyes.

Moreover, it has a strong initial stimulation not being aversion effect due to contact or taking in, its antibacterial and antifungal effects and aversion effect on vermin are good enough to prevent from surface contamination or rottenness of compositions after installation of bird aversion agent, and thus it is useful to stop decreasing of the effect of bird aversion agent.

The cinnamon essential oil is used within a range from 0.1 to 10% by weight per the total weight of the composition, and preferably a range from 1 to 5% by weight.

At this time, if the cinnamon essential oil is used in an amount equal to or less than 0.1% by weight per the total weight of the composition, then its antibacterial and antifungal effects are decreased to cause contamination of the composition with bacteria and fungus, and if it is used in an amount equal to or greater than 10% by weight, then its viscosity can be decreased.

The mint essential oil as one of main ingredients of the present invention contains mentol as a main active ingredient, and it may represent an osmatic aversion effect caused by strong irritable volatile scents as well as an aversion effect caused by stimulation of mucous membranes in eyes.

Moreover, it has a strong initial stimulation not being aversion effect due to contact or taking in, its antibacterial and antifungal effects and aversion effect on vermin are good enough to prevent from surface contamination or rottenness of compositions after installation of bird aversion agent, and thus it is useful to stop decreasing of the effect of bird aversion agent.

The mint essential oil is used within a range from 0.1 to 20% by weight per the total weight of the composition, and preferably a range from 1 to 10% by weight.

At this time, if the mint essential oil is used in an amount equal to or less than 0.1% by weight per the total weight of the composition, then its antibacterial and antifungal effects can be decreased, and if it is used in an amount equal to or greater than 20% by weight, its viscosity can be decreased.

Accessory components of the bird aversion composition according to the present invention include proper amounts of emulsifier and a stabilizer.

Mineral oil or grease can be used as the above mentioned stabilizer, the mineral oil or grease may form oil layer on the surface of bird aversion composition to prevent moisture from penetrating into bird aversion composition in areas having humid weather such as snow or rain, it can stop loss of main ingredients in bird aversion agent or its denaturation to keep up the stability of bird aversion composition and to continue its aversion effect.

The mineral oil or grease is used within a range from 5 to 40% by weight per the total weight of the composition, and preferably a range from 15 to 30% by weight.

At this time, if the mineral oil or grease used in an amount equal to or less than 5% by weight per the total weight of the composition, then the formation of oil layer may be unstable to make loss of composition, and if it is used in an amount equal to or greater than 40% by weight, its viscosity may be decreased to reduce bird aversion effect.

Moreover, sorbitan esters of fatty acids may be used as emulsifier, which have been already used to emulsify and disperse pigment, printing ink, paint, fiber coarse material, lubricant and the like industrially, the emulsifier is used for the purpose of dispersing plant essence as a main ingredient of bird aversion composition and methyl anthranilate in the entire composition.

The sorbitan esters of fatty acids may be used as a mixture of one or two selected from the group consisting of sorbitan monolaurate, sorbitan monopalmitate, sorbitan monooleate, sorbitan monostearate, and sorbitan monobehenate according to kinds of fatty acids.

A mixed solution of sorbitan monolaurate and sorbitan monooleate may be used, and the mixed solution contains 10 to 40% by weight of sorbitan monolaurate and 60 to 90% by weight of sorbitan monooleate.

The emulsifier is used within a range from 1 to 10% by weight per the total weight of the composition, and preferably a range from 2 to 6% by weight.

At this time, if the emulsifier is used in an amount equal to or less than 1% by weight per the total weight of the composition, then the emulsifying degree of mint essential oil and cinnamon essential oil may be decreased not to mix in the composition thoroughly, and if it is used in an amount equal to or greater than 10% by weight, its viscosity can be decreased to reduce bird aversion effect and loss inhibiting effect of the Mode for Invention Now, the following non-limiting examples are used to further describe or illustrate the invention. The examples are given for illustration of the invention and are not intended to be limiting thereof.

EXAMPLES

Example 1

Preparation of Bird Aversion Composition

Cinnamon essential oil, mint essential oil, emulsifier were equally mixed in a mixer, and then mixed with the added UV absorbent and methyl anthranilate. Finally, polybutane and grease were added thereto and mixed thoroughly to obtain a bird aversion composition.

The contents of the used respective ingredients were 65% by weight of polybutane, 25% by weight of grease, 0.5% by weight of Ciba™ TINUVIN™ 99-2, 3% by weight of methyl anthranilate, 0.5% by weight of cinnamon essential oil, 1% by weight of mint essential oil and 5% by weight of sorbitan monooleate.

Example 2

Preparation of Bird Aversion Composition

65% by weight of polybutane, 25% by weight of grease, 0.5% by weight of Ciba™ TINUVIN™ 99-2, 3% by weight of methyl anthranilate, 1.5% by weight of cinnamon essential oil, 2% by weight of mint essential oil and 2% by weight of sorbitan monooleate were used to obtain a bird aversion composition using the same method as in Example 1.

Example 3

Preparation of Bird Aversion Composition and Procedures Thereof

65% by weight of polybutane, 25% by weight of grease, 0.5% by weight of Ciba™ TINUVIN™ 99-2, 4% by weight of methyl anthranilate, 1.5% by weight of cinnamon essential oil, 3% by weight of mint essential oil and 1% by weight of sorbitan monooleate were used to obtain a bird aversion composition using the same method as in Example 1.

Test Example 1

Bird Aversion Effect According to Bird Aversion Composition

To evaluate a bird aversion effect of a bird aversion composition prepared in Examples, the bird aversion effect of the subject Bengalee in Order Passeriformes Family Estrildidae was identified in a laboratory scale, in which the Bengalee was active and moved a lot. The number of times of landing on roost and abnormal behavior of Bengalee was observed after applying a bird aversion composition composed according to Examples on a roost.

After Bengalee exposed to a bird aversion composition prepared in Examples which has been applied on roost, they didnt try to land, and the individuals contacting the bird aversion composition showed good bird aversion effect representing abnormal behaviors such as wiping, head shaking, piloerection, quick-preening and heavy shaking of the contacted areas.

However, a bird aversion composition prepared in Example 3 had a good physical property such as viscosity, when it was applied on roost, the least lost of bird aversion composition due to flowing down or contacting target birds was observed.

Test Example 2

Evaluation of Efficacy of Bird Aversion Composition on Order Passeriformes Aquarium Birds 1. A Test Method
1) Noticed Animals Zibrafinch and Bengalee in Order Passeriformes Family Estrildidae were used in a laboratory scale to confirm a bird aversion effect. Zibrafinch and Bengalee have been broadly raised as cage birds in Korea, and thus they may be easily used for experiments. Because they were active and moved a lot and they showed easily bird aversion effect and whether they were adapted or not, they were noticed as test animals 2) Raising Environment Male Zibrafinch (n=10) and male Bengalee (n=15) were purchased from a bird farm near Daejeon city, and were noticed for the test by selecting healthy individuals randomly through an acclimation period of a week under a laboratory condition (20 to 22° C. of temperature, 50 to 70% of humidity and 0:00 to 06:00 h of dark period).

Test raising box having a scale of 50×150×50 cm of width× length×height was used, and food and water were fed freely.

3) Evaluation of an Aversion Effect of a Bird Aversion Composition

In order to verify an aversion effect of the bird aversion composition prepared according to Example 3, the number of times of landing on ground and roost was observed after an acclimation period of a week under a laboratory condition, by using video camera (Everio G series, JVC, Japan) for 24 hours.

The number of times of landing on ground and roost was observed again by using video camera for 24 hours after applying the bird aversion composition prepared in Example 3 on roost. Whether visual abnormal behaviors of the target bird on scent and contact test material or not was determined by observing Birds reactions such as wiping, head shaking, piloerection, quick-preening and heavy shaking of the contacted areas.

4) Determination of Acclimation to a Bird Aversion Composition

In order to verify whether an acclimation of the bird aversion composition prepared in Example 3 after a contact or not, the number of times of landing on ground and roost was observed by using video camera for 24 hours after moving the noticed animal exposed to the bird aversion composition for 24 hours to the raising box not applied with the bird aversion composition again, acclimating for a week, checking its normal flying activity, and then moving it to the raising box applied with the bird aversion composition.

Learning effect of the noticed bird and whether an adaptation or not of a bird aversion agent were checked by repeating an exposure to a bird aversion composition 4 times with a week interval. Whether visual abnormal behaviors of the target bird on scent and contact test material or not was determined by observing Birds reactions such as wiping, head shaking, piloerection, quick-preening and heavy shaking of the contacted areas.

2. Results of an Experiment

1) An Aversion Effect of a Bird Aversion Composition

Most of Zibrafinch sat in turns on roost, a feed bucket, and a water pail, showed a normal flying activity before applying a bird aversion composition during acclimation period and after completion of acclimation.

But, all of individuals contacted a bird aversion composition landed on the ground after applying the bird aversion composition as showed in FIG. 1, some individuals tried to land on roost, but they all stayed only on the ground after an exposure of 30 min. Some individuals contacted a bird aversion composition showed abnormal behaviors such as squatting, wiping, head shaking, quick-preening and heavy shaking of the contacted areas. Therefore, we found that the bird aversion composition of the present invention showed a good bird aversion effect.

2) Acclimation to a Bird Aversion Composition

In the cases of exposing the noticed animals to a bird aversion composition once, checking their normal flying activities and recovering of behavioral patterns in the raising box not applied with the bird aversion composition for a week, and exposing them the bird aversion composition again, all the noticed animals didn't contact the bird aversion composition, and landed on the floor not to sit on roost.

They just moved intermittently to floor, a feed bucket, and a water pail, but didn't land on the roost applied with a bird aversion composition. Such a result showed that Zibrafinch had already recognized strong smell and ultraviolet ray absorbent contained in the bird aversion composition sat on the floor by an experience of contacting a bird aversion composition, individuals adapted to bird aversion composition were not observed even by a continued exposure of a bird aversion composition and a repetition of acclimation.

All of the noticed animals recognized a bird aversion composition by learning effect of an exposure of a bird aversion composition, they never sat on the roost applied with bird aversion compositions again, and aversion effects were not adapted to repeated exposures of these bird aversion compositions.

Therefore, an adaptation of bird aversion compositions of the present invention to repeated exposures was not observed, and a good bird aversion effect by learning effect was observed.

Test Example 3

Evaluation of real bird aversion effect of bird aversion composition in zoo contaminated by doves 1. An Experiment Method We selected a zoo having external buildings contaminated seriously by excrements of doves and the like, installed the bird aversion composition prepared in Example 1 on it, and evaluated its bird aversion effect.

2. Results of an Experiment

Most of seriously contaminated buildings had projecting parts therein on which doves could land, and they had proper structures as a mid resting place and a shelter being able to avoid wind and rain Building floor and projecting parts were contaminated seriously by excrements as showed in FIG. 2 before operating a bird aversion composition As illustrated in FIG. 3, the number of homing doves was significantly decreased on the first day after an installation of a bird aversion composition, and we observed that the homing doves couldn't land on the projected parts installed with a bird aversion composition, and they made a circular flight, and flied to other places.

Landing trial and homing of birds were never observed from the third day after an installation of a bird aversion composition. Homing of birds was not observed in three months after an installation of a bird aversion composition, and excrement contamination due to homing of doves was not observed.

Therefore, the present invention had a good bird aversion effect of a bird aversion composition, and also showed a long-term effect compared to the prior art, bird aversion agent.

The invention claimed is:
1. A gel-type bird aversion composition, comprising:
   30 to 90% by weight of polybutene;
   0.01 to 4% by weight of an ultraviolet ray absorbent selected from the group consisting of benzophenones, benzotriazoles, salicylates, cyanoacrylates, and oxanilides;
   0.1 to 20% by weight of methyl anthranilate;
   0.1 to 10% by weight of cinnamon essential oil;
   0.1 to 20% by weight of mint essential oil;
   5 to 40% by weight of mineral oil or grease; and
   1 to 10% by weight of sorbitan esters of fatty acids.

* * * * *